US00RE34466E

United States Patent [19]

Taylor et al.

[11] E Patent Number: Re. 34,466

[45] Reissued Date of Patent: Dec. 7, 1993

[54] EXTENDABLE GUIDEWIRE FOR CARDIOVASCULAR PROCEDURES

[75] Inventors: Charles S. Taylor, San Francisco; Robert M. Abrams, Mountain View; Kirsten L. Valley, Belmont; Beverly Huss, Santa Clara; Craig E. Mar, Fremont; Jeffrey L. Kraus, San Jose; Linda T. Guthrie, Fremont, all of Calif.

[73] Assignee: Advanced Cardiovascular Systems, Inc., Santa Clara, Calif.

[21] Appl. No.: 979,469

[22] Filed: Nov. 20, 1992

Related U.S. Patent Documents

Reissue of:

[64] Patent No.: 4,827,941
Issued: May 9, 1989
Appl. No.: 137,963
Filed: Dec. 23, 1987

U.S. Applications:

[63] Continuation of Ser. No. 697,780, May 9, 1991, abandoned.

[51] Int. Cl.[5] ..... A61B 6/00

[52] U.S. Cl. ..... 128/657; 128/772; 604/164; 140/111; 29/453; 29/525

[58] Field of Search ..... 128/657, 772, 200.26; 604/164, 166, 170, 282; 140/111; 29/453, 525; 439/825, 826, 827

[56] References Cited

U.S. PATENT DOCUMENTS

| | | | |
|---|---|---|---|
| 3,400,447 | 9/1968 | Woods, Jr. et al. | 29/525 |
| 4,003,369 | 1/1977 | Heilman et al. | 128/772 |
| 4,045,859 | 9/1977 | Cooley et al. | 29/525 |
| 4,068,660 | 1/1978 | Beck | 604/158 |
| 4,538,622 | 9/1985 | Samson et al. | 128/772 |
| 4,554,800 | 11/1985 | Moon | 63/13 |
| 4,569,347 | 2/1986 | Frisbie | 128/344 |
| 4,617,715 | 10/1986 | Koistinen et al. | 29/525 |
| 4,875,489 | 10/1989 | Messner et al. | 128/657 |
| 4,922,923 | 5/1990 | Gambale et al. | 128/657 |

FOREIGN PATENT DOCUMENTS

| | | | |
|---|---|---|---|
| 2180454 | 4/1987 | United Kingdom | 128/772 |

OTHER PUBLICATIONS

"Guide Wire Extension", by C. Cope, M.D. *Radiology* 1985; 157; 263 Sep. 24, 1985.

*Primary Examiner*—Randy C. Shay
*Attorney, Agent, or Firm*—Fulwider, Patton, Lee & Utecht

[57] ABSTRACT

An extendable guidewire system for introducing a dilatation catheter into the cardiovascular system. The guidewire has guidewire and extension sections with a connection therebetween which permits the two sections to be joined together and separated simply by pushing the two sections together and pulling them apart. One of the sections can be used for positioning the catheter within the cardiovascular system, and the other section can be employed to extend the wire to change catheters.

31 Claims, 1 Drawing Sheet

EXTENDABLE GUIDEWIRE FOR CARDIOVASCULAR PROCEDURES

Matter enclosed in heavy brackets [ ] appears in the original patent but forms no part of this reissue specification; matter printed in italics indicates the additions made by reissue.

*This application is a continuation, of application Ser. No. 07/697,780 filed May 9, 1991, now abandoned.*

BACKGROUND OF THE INVENTION

This invention generally relates to cardiovascular procedures such as angioplasty, angiography and valvuloplasty, and more particularly to an extendable guidewire for use in such procedures.

Guidewires are currently used to facilitate the placement of catheters in the arterial system of a patient for cardiovascular procedures such as angioplasty, angiography and valvuloplasty. The guidewire is typically on the order of 20–50 cm longer than the catheter to permit the guidewire and the catheter to be advanced relative to each other as they are steered into position within the patient's body. Suitable guidewires are described in U.S. Pat. No. 4,538,622 (Samson et al.) and U.S. Pat. No. 4,569,347 (Frisbie) which are hereby incorporated herein in their entirety.

In the usual procedure to change catheters, the guidewire is removed from the patient, and an exchange wire is inserted in its place. The in-place catheter is removed from the patient and a new catheter is inserted into the patient. The exchange wire is then removed and the guidewire is reinserted. The exchange wire is substantially longer than the guidewire, and it generally extends outside the patient's body for a distance greater than the length of the catheter. With a dilatation catheter having a length on the order of 120–140 cm, for example, a guidewire might have a length on the order of 175 cm, and an exchange wire might have a length on the order of 300 cm. The use of an exchange wire has the obvious disadvantage that it complicates the angioplasty procedure.

Heretofore, there have been some attempts to eliminate the need for a separate exchange wire by attaching an extension wire to a guidewire to extend the length thereof. The two wires are joined together by a crimped connector which requires a special tool. Once the wires have been crimped, the connection therebetween is permanent, and the extension wire cannot be removed except by severing it from the guidewire.

What has been needed and heretofore unavailable is an extension which can be readily connected and disconnected to the guidewire when it is in position within the patient. The present invention satisfies this need.

SUMMARY OF THE INVENTION

The present invention provides a new and improved guidewire system and the method of using the same.

In accordance with the present invention, a guidewire is provided with main and extension sections which are detachably secured together by press fitting. One of the guidewire sections has a tubular portion at the connecting end thereof, and the other guidewire section has a connecting end portion which has an effective diameter in one radial dimension which is slightly larger than the inner diameter of the tubular portion. The slightly larger connecting end of one of the guidewire sections is inserted into the tubular end of the other guidewire section. One or both of the connecting ends are deformed to provide an interference or friction fit therebetween and thereby detachably secure the two guidewire sections together. The two sections can be readily separated by pulling them apart. The two sections can be reconnected and disconnected as desired.

In the presently preferred embodiment, the end portion of the male end of the connection has an undulating shape which is adapted to be inserted into the tubular end of the guidewire section. The effective diameter of the undulating portion should not be more than 50% greater than the inner diameter of the tubular member to facilitate the insertion and removal thereof from the tubular member.

These and other advantages of the invention will become more apparent from the following detailed description thereof and the accompanying exemplary drawings.

DETAILED DESCRIPTION OF THE INVENTION

Figures 1, 2, 3, 4:
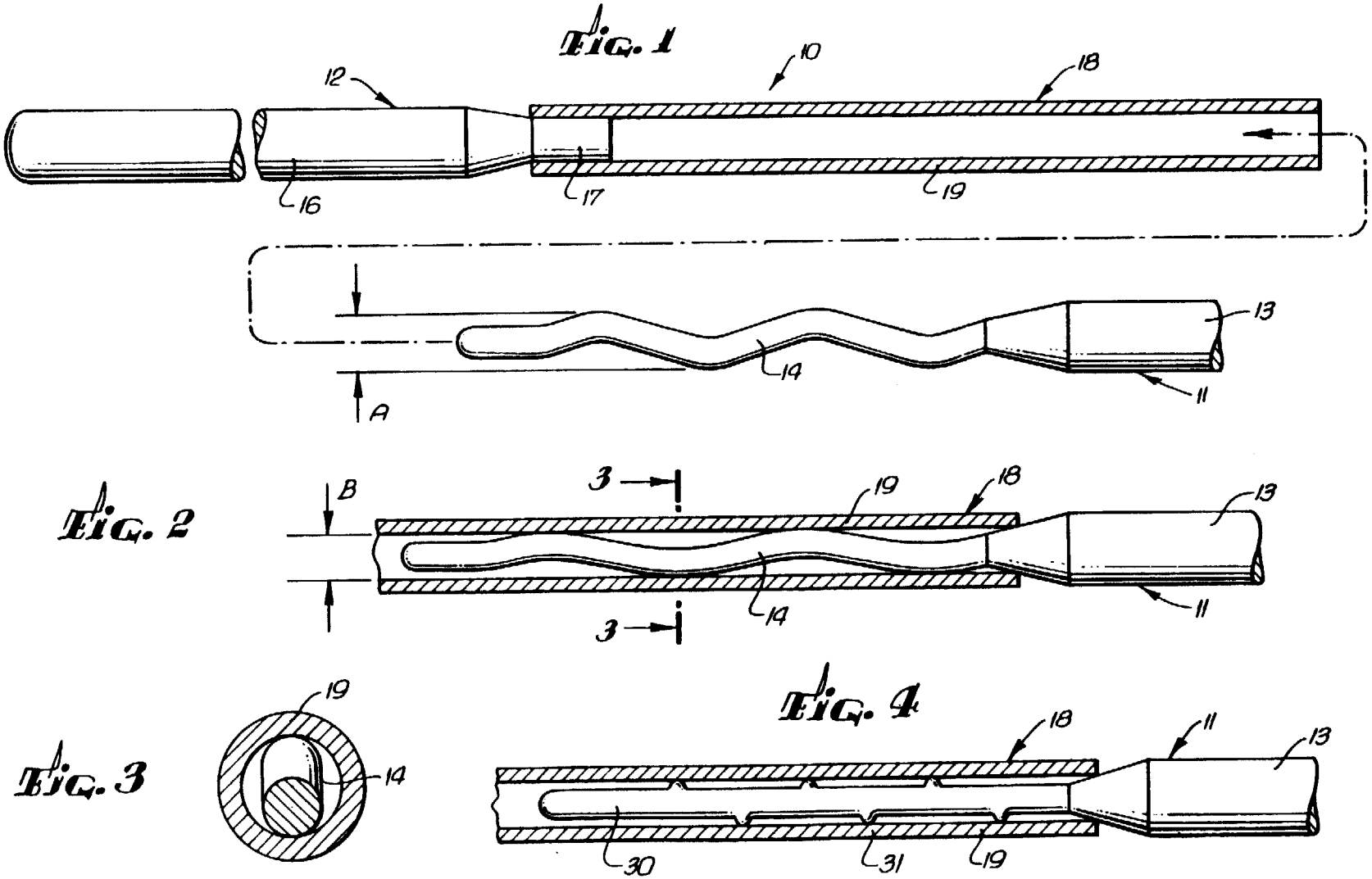
FIG. 1 is a fragmentary, centerline sectional view of an extendable guidewire embodying features of the invention, with parts separated.
FIG. 2 is a fragmentary centerline view of the embodiment shown in FIG. 1 with the parts joined.
FIG. 3 is a cross-section view taken along lines 3–3 of FIG. 2.
FIG. 4 is a partial centerline sectional view of an alternative embodiment.

As illustrated in FIG. 1–3, the guidewire system 10 embodying features of the invention has a main section 11 which is adapted to be inserted into a patient's vascular system and an extension section 12 which can be connected and disconnected to the main section 11 to facilitate the exchange of catheters without the need for removing the main section 10 from the patient's vascular system. Main guidewire 11 generally comprises an elongated shaft 13 with a flexible tip (not shown) at its distal end and a smaller diameter portion 14 at its proximal end which is shaped into an undulating or sinusoidal shape. Reference is made to U.S. Pat. No. 4,538,622 (Samson et al.) and U.S. Pat. No. 4,569,347 (Frisbie), which have been previously incorporated herein by reference, for a description of desirable guidewire tip constructions. Extension section 12 has an elongated shaft 16 with smaller diameter projection or post 17 at its distal end.

The connection 18 between guidewire sections 11 and 12 generally comprise tubular member 19 which is fixed to the distal end of the main section 12 and which receives interfitting undulating member 14 which is on the proximal end of section 11. Tubular member 19 is mounted by suitable means such as welding, brazing, or the like onto the short axial extension 17 of reduced diameter at the distal end of shaft 16. Axial extension or post 17 can be formed by any suitable means such as grinding down the proximal end portion of the shaft 16 to the desired diameter so that it interfits into the end of tubular member 15. The undulating portion 14 is formed by first grinding the proximal end of main section 11 to a smaller diameter, then forming the undulations or sinusoidal shape by bending over a mandrel or other suitable means. The maximum effective dimension A of the undulated section should be slightly more than the inner diameter B of tubular connecting piece 17 but preferably not more than 50% greater than dimension B to provide interference or friction fit which will hold the sections together during catheter exchange but which can be readily disengaged after exchange has been made. Preferably no more than a one pound pull should be necessary for disengagement.

In a guidewire having a diameter on the order of about 0.014 inch, for example, tubular member 19 might have an inner diameter of about 0.007 inch and a wall thickness on the order of 0.001 inch and the undulating section 14 might have a maximum effective radial dimension of about 0.009 inch. In this embodiment, tubular member 19 might have a length on the order of about 2.4–2.5 cm.

The main guidewire section is intended for use in positioning a dilatation catheter (not shown) in the cardiovascular system of a patient, and it has a length corresponding to the length of a conventional guidewire for this purpose. Details of typical dilatation catheters and guidewires can be found in the patents cited previously and incorporated herein.

Extension section 12 is sufficiently long so that when the guidewire sections 11 and 12 are connected together the guidewire system 10 has an overall length suitable for exchanging catheters without removing the main section 11 from the patient's vascular system. With a dilatation catheter having a length on the order of 120–140 cm, for example, section 11 might have a length of 140–175 cm, and section 12 might have a length of 125–160 cm.

Shafts 13 and 16 and tubular member 19 can be fabricated from suitable material, such as stainless steel, Nitinol (55% NI-Bal. Ti), and the like, and each should have a diameter to allow a dilatation catheter to pass freely over them. It is perferably that the two shafts 13 and 16 be of substantially the same diameter in order to provide a smooth transition between them. In one presently preferred embodiment for use in coronary angioplasty, shafts 13 and 16 have a diameter on the order of about 0.014 inch. Either or both of the shafts can be provided with a coating of polytetrafluoroethylene, which is sold under the trademark Teflon by the DuPont Corporation, or another suitable low-friction material to facilitate the movement of the catheter over the wire.

An alternative embodiment is shown in FIG. 4 wherein the proximal end of main guidewire section 12 which is adapted to be inserted into the tubular member 19 is provided with a smaller diameter portion 30 having protrusions 31 which provide the interference or friction fit to releasably secure together the sections 11 and 12 of the guidewire system 10. The protrustions can have various shapes such as the semi-spherical shapes shown in FIG. 4, triangular shapes, or other shapes which may provide a suitable fit.

In use, the main guidewire section 11 is introduced into the vascular system of a patient with a dilatation catheter through a guiding catheter not shown) and an introducer (not shown). When performing coronary angioplasty, the distal end of the guiding catheter is positioned in the coronary ostium, and the dilatation catheter is advanced so that it is just proximal to the tip of the guiding cathether.

The distal tip of the guidewire is advanced beyond the distal tip of the dilatation catheter while the latter is held in place. As the main guidewire section 11 is advanced, it is rotated and steered into the selected artery. The guidewire tip is preferably advanced through the lesion and beyond it, in order to permit the balloon portion of the dilatation catheter to be positioned within the lesion over a more supportive section of the guidewire. Once in position, the main guidewire section 11 is held in place and the dilatation catheter is advanced along it until the inflatable balloon thereof is within the lesion. Undulating end portion 14 remains outside the patient's body and outside any adapter which may be connected to the proximal end of the dilatation catheter.

To exchange catheters, the main guidewire section 11 is extended by manually pressing the open end of tubular member 19 on the distal end of extension section 12 onto the undulating end 14. As the tubular member 19 is inserted over the undulating end 14, either the tubular member 19 or the undulating member 14 or both deform to thereby firmly but releasably hold the two guidewire sections together. The dilatation catheter can then be withdrawn from the patient's body over the extended guidewire system.

A new dilatation catheter may then be introduced over the extension section 12 and advanced along the main guidewire section 11 within the patient's body until the balloon crosses the lesion. Once the proximal end of the new balloon catheter has advanced beyond connection 18 and tubular end portion 19, section 12 can be removed by grasping the two guidewire sections 11 and 12 on opposite sides of the connection 18 and pulling them apart without disturbing the position of section 11 in the patient's body. As previously described, the interference or friction fit between the undulating member 14 and the tubular member 19 should be sufficiently strong to hold the two guidewire sections 11 and 12 together while dilatation catheters are being exchanged, but should be capable of separation by a pulling force less than one pound.

The invention has a number of important features and advantages. The two sections of the guidewire can be connected together whenever a longer wire is needed, and they can be separated whenever the additional length is not required. The two sections of the guidewire may be connected and disconnected by the physician by simply pressing them together and pulling them apart. This can be done as needed, and no special tools are required either to make the connection or to separate it. Thus the catheter exchange is greatly simplified.

It is apparent from the foregoing that a new and improved extended guidewire system and method of using the same have been provided. While the present invention has been described herein with the tubular connecting element fixed to the distal end of the guidewire extension section and the male member adapted to be inserted into the open end of the tubular member on the proximal end of the main guidewire section, it is obvious that the tubular element on the distal end of the extension section may be interchanged with the male member on the main guidewire section. Moreover, it will be apparent to those familiar with the art, that other modifications and improvements can be made without departing from the scope of the invention as defined by the following claims.

What is claimed is:

1. An extendable guidewire system comprising:

(a) a main guidewire section adapted to be inserted into a patient's vascular system which has a mating end adapted to extend out of the patient;

(b) a guidewire extension section having a mating end; and (c) a connection therebetween suitable for repetitive connections including a tubular member on the mating end of one of the guidewire sections having an open end, a male member on the mating end of the other guidewire section which is adapted to be manually inserted into the open end of the tubular member and means to releasably secure the two sections together by frictional engagement between the tubular member and the male member.

2. The extendable guidewire system of claim 1 wherein the tubular member is fixed to the mating end of the guidewire extension section and the male member is on the mating end of the main guidewire section.

3. The extendable guidewire system of claim 1 wherein the tubular member is fixed to the mating end of the main guidewire section and the male member is on the mating end of the guidewire extension section.

4. The guidewire extension system of claim 1 wherein the tubular member is fixed to an end of a guidewire section by welding.

5. The guidewire extension system of claim 1 wherein the tubular member is fixed to an end of a guidewire section by brazing.

6. The guidewire extension system of claim 1 wherein the male member has protrusions on the outer surface thereof which engage the inner surface of the tubular member to thereby releasably secure the two guidewire sections together.

7. The extendable guidewire system of claim 1 wherein the male member has a diametrical dimension slightly larger than the inner diametrical dimension of the tubular member receiving the male member so that upon the insertion of the male member into the tubular member the guidewire sections are releasably secured together.

8. The extendable guidewire system of claim 7 wherein the male member is provided with an undulated shape.

9. The extendable guidewire system of claim 7 wherein the maximum diametrical dimension of the male member is not more than 50% greater than the inside diameter of the tubular member.

10. A method of using an extendable guidewire system in a vascular procedure, said guidewire system having a main guidewire section with a mating end, a guidewire extension section with a mating end, and a connection therebetween suitable for repetitive connections comprising a tubular member having an open end on one of said mating ends of the guidewire sections, a male member on the mating end of the other section which is adapted to be inserted into the open end of the tubular member and means to releasably secure the interconnected ends together, the method comprising the steps of:

(a) percutaneously introducing a main guidewire section into the vascular system of a patient with the mating end thereof extending outside the body of the patient;

(b) advancing a first catheter over the main guidewire section within the vascular system;

(c) releasably securing the mating end of the extension guidewire section to the mating end of the main guidewire section by manually inserting the male member on one of the guidewire sections into the tubular member on the other guidewire section so that the interconnected ends are releasably secured together by frictional engagement between the tubular member and the male member;

(d) withdrawing the first catheter from the vascular system of the patient over the two interconnected guidewire sections;

(e) introducing a second catheter into the patient's vascular system over the two interconnected guide sections; and (f) disengaging the extension guidewire section from the main guidewire section by manually pulling the two guidewire sections apart with the main guidewire section remaining in place in the vascular system of the patient.

*11. An extendable guidewire system for multiple catheter exchanges, comprising:*

*a. a main guidewire section adapted to be inserted into a patient's vascular system, said guidewire section having a mating end adapted to extend out of the patient;*

*b. a guidewire extension section having a mating end; and*

*c. connecting means for repetitive connections between said main guidewire section and said extension section by non-permanent deformation of either of said mating end whereby said extension wire section and said main guidewire section can be repetitively connected and disconnected.*

*12. The extendable guidewire system of claim 11 wherein the maximum diameter of said connection means, after connection, is substantially the same diameter as that of said main guidewire section.*

*13. The extendable guidewire system of claim 11 wherein one of said mating ends is composed of elastically deformable material.*

*14. The extendable guidewire system of claim 11 wherein said connecting means includes a tubular member on the mating end of one of the guidewire sections, said tubular member having an open end, and a male member on the mating end of the other guidewire section.*

*15. The extendable guidewire system of claim 14 wherein said male member is adapted to be inserted into said open end of said tubular member.*

*16. The extendable guidewire system of claim 14 wherein said tubular member and said male member are releasably secured at their mating ends by frictional engagement.*

*17. An extendable guidewire system for multiple catheter exchanges, comprising:*

*a. a main guidewire section adapted to be inserted into a patient's vascular system, said guidewire section having a mating end adapted to extend out of the patient;*

*b. a guidewire extension section having a mating end;*

*c. connecting means for detachably joining said mating end of said main guidewire section to said mating end of said guidewire extension section, said connecting means including a tubular member on the mating end of one of the guidewire sections, said tubular member having an open end, and a male member on the mating end of the other guidewire section adapted for slidable insertion into said tubular member; and*

*d. said connecting means having a maximum diameter, after connection, no greater than the maximum diameter of said tubular member.*

*18. An extendable guidewire system for multiple catheter exchanges, comprising:*

*a. a main guidewire section adapted to be inserted into a patient's vascular system, said guidewire section having a mating end formed by a tubular member adapted to extend out of the patient;*

*b. a guidewire extension section having a mating end;* c. connecting means for detachably joining said mating end of said main guidewire section to said mating end of said guidewire extension section; and d. said connecting means having an overall maximum diameter, after connection, no greater than the maximum diameter of said tubular member.

19. An extendable guidewire system for multiple catheter exchanges, comprising:

a. a main guidewire section adapted to be inserted into a patient's vascular system, said guidewire section having a mating end adapted to extend out of the patient;

b. a guidewire extension having a mating end formed by a tubular member;

c. connecting means for detachably joining said mating end of said main guidewire section to said mating end of said guidewire extension section; and d. said connecting means having an overall maximum diameter, after connection, no greater than the maximum diameter of said tubular member.

20. An extendable guidewire system for multiple catheter exchanges, comprising:

a. a main guidewire section adapted to be inserted into a patient's vascular system, said guidewire section having a mating end formed by a tubular member adapted to extend out of the patient;

b. a guidewire extension having a mating end;

c. connecting means for detachably joining said mating end of said main guidewire section to said mating end of said guidewire extension section; and d. at least a portion of said connecting means having an overall maximum diameter, prior to connection, greater than the inside diameter of said tubular member.

21. An extendable guidewire system for multiple catheter exchanges, comprising:

a. a main guidewire section adapted to be inserted into a patient's vascular system, said guidewire section having a mating end adapted to extend out of the patient;

b. a guidewire extension having a mating end formed by a tubular member;

c. connecting means for detachably joining said mating end of said main guidewire section to said mating end of said guidewire extension section; and d. at least a portion of said connecting means having an overall maximum diameter, prior to connection, greater than the inside diameter of said tubular member.

22. The extendable guidewire system of claim 21 wherein one of said mating ends has a diametrical dimension larger than the inner diametrical dimension of the other said mating end so that upon insertion of one mating end into the other mating end the corresponding guidewire sections are releasably secured together.

23. An extendable guidewire system for multiple catheter exchanges, comprising:

a. a main guidewire section adapted to be inserted into a patient's vascular system, said guidewire section having a mating end adapted to extend out of the patient;

b. a guidewire extension section having a mating end; and c. connecting means for repetitive connections between said main guidewire section and said extension section by non-permanent deformation of either of said mating ends whereby said mating end of said extension wire section changes length along its longitudinal axis when connected and disconnected to said main guidewire section.

24. An extendable guidewire system for multiple catheter exchanges, comprising:

a. a main guidewire section adapted to be inserted into a patient's vascular system, said guidewire section having a mating end adapted to extend out of the patient;

b. a guidewire extension section having a mating end;

c. connecting means for repetitive connections between said guidewire section and said extension section by the non-permanent deformation of either of said mating ends; and d. means responsive to relative longitudinal movement of said connecting means for yieldably reducing the overall diameter of said mating end of said extension section.

25. The extendable guidewire system of claim 24 wherein one of said mating ends is made of elastically deformable material.

26. An extendable guidewire system for multiple catheter exchanges, comprising:

a. a main guidewire section adapted to be inserted into a patient's vascular system, said guidewire section having a mating end adapted to extend out of the patient;

b. a guidewire extension section having a mating end;

c. resilient, selectably releasable connecting means for repetitive connections between said main guidewire section and said extension section by the non-permanent deformation of either of said mating ends whereby said extension wire section and said main guidewire section can be repetitively connected and disconnected.

27. The extendable guidewire system of claim 26 wherein one of said mating ends is made of elastically deformable material.

28. An extendable guidewire system for multiple catheter exchanges, comprising:

a. a main guidewire section adapted to be inserted into a patient's vascular system, said guidewire section having a mating end adapted to extend out of the patient;

b. a guidewire extension section having a mating end;

c. connecting means for repetitive connections between said main guidewire section and said extension section by non-permanent deformation of either of said mating ends; and d. resilient spring means provided by one of said mating ends for imparting a retaining force to said other mating end after said mating ends are releasably connected.

29. An extendable guidewire system for multiple catheter exchanges, comprising:

a. a main guidewire section adapted to be inserted into a patient's vascular system, said guidewire section having a mating end adapted to extend out of the patient;

b. a guidewire extension section having a mating end;

c. one of said mating ends adapted to receive the other mating end to provide a detachable connection; and d. resilient spring means within said connection for retaining said mating ends in detachable engagement.

30. A method of using an extendable guidewire system in a vascular procedure, said guidewire system having a main guidewire section with a mating end, a guidewire extension section with a mating end, and a connection therebetween suitable for repetitive connections comprising a tubular member having an open end on one of said mating ends of the guidewire sections, a male member on the mating end of the other section which is adapted to be inserted into the open end of the tubular member and means to releasably secure the interconnected ends together, the method comprising the steps of:

*a. percutaneously introducing a main guidewire section into the vascular system of a patient with the mating end thereof extending outside the body of the patient;*

*b. advancing a first catheter over the main guidewire section within the vascular system;*

*c. releasably securing the mating end of the extension guidewire section to the mating end of the main guidewire section by manually inserting the male member on one of the guidewire sections into the tubular member on the other guidewire section so that the interconnected ends are releasably secured together by a spring force between said male member and the inner surface of said tubular member;*

*d. withdrawing the first catheter from the vascular system of the patient over the two interconnected guidewire sections;*

*e. introducing a second catheter into the patient's vascular system over the two interconnected guidewire sections; and*

*f. disengaging the extension guidewire section from the main guidewire section by manually pulling the two guidewire sections apart with the main guidewire section remaining in place in the vascular system of the patient.*

*31. An extendable guidewire system for multiple catheter exchanges, comprising:*

*a. a main guidewire section adapted to be inserted into a patient's vascular system, said guidewire section having a mating end adapted to extend out of the patient;*

*b. a guidewire extension having a mating end formed by a tubular member;*

*c. connecting means for detachably joining said mating end of said main guidewire section to said mating end of said guidewire extension section; and*

*d. said connecting means having an overall maximum diameter, after connection, no greater than the maximum diameter of either of said guidewire extension section or main guidewire section.*

* * * * *

UNITED STATES PATENT AND TRADEMARK OFFICE

CERTIFICATE OF CORRECTION

PATENT NO. : Re. 34,466

DATED : December 7, 1993

INVENTOR(S) : Charles S. Taylor, Robert M. Abrams, Kirsten L. Valley, Beverly Huss, Craig E. Mar, Jeffrey L. Kraus and Linda T. Guthrie It is certified that error appears in the above-indentified patent and that said Letters Patent is hereby corrected as shown below:

Column 6, line 55, change "of one of the guidewire sections, said tubular member" to --of either said main guidewire section or said guidewire section, said tubular member--.

Column 6, line 57, change "the other guidewire" to --said guidewire--.

Column 6, line 57, change "section adapted" to --section to which said tubular member is not connected, the male member being adapted--.

Signed and Sealed this

Ninth Day of July, 1996

*Attest:*

Bruce Lehman

BRUCE LEHMAN

*Attesting Officer*

*Commissioner of Patents and Trademarks*